|   |   |   |
|---|---|---|
| United States Patent [19] | [11] Patent Number: | 4,849,211 |
| Schrauzer | [45] Date of Patent: | Jul. 18, 1989 |

[54] PRODUCT AND METHOD FOR THE TREATMENT OF ACNE AND OTHER SKIN DISORDERS

[76] Inventor: Gerhard N. Schrauzer, 175 Alameda Blvd., Coronado, Calif. 92118

[21] Appl. No.: 168,934

[22] Filed: Mar. 16, 1988

[51] Int. Cl.$^4$ .................................................. A61L 9/04
[52] U.S. Cl. ........................................ 424/45; 424/69; 424/70; 424/642; 514/178; 514/744; 514/762; 514/844; 514/846; 514/884
[58] Field of Search ...................... 424/45, 69, 70, 145; 514/178, 625, 884, 844, 744, 846, 762, 625

[56] References Cited

U.S. PATENT DOCUMENTS

| 3,046,199 | 7/1962 | Suzuki ................................... 424/45 |
| 3,312,591 | 4/1967 | Elks ....................................... 424/45 |
| 3,860,712 | 1/1975 | Ferrari ................................. 514/171 |
| 3,883,661 | 5/1975 | Young .................................. 514/625 |
| 4,021,572 | 5/1977 | Van Scott ........................... 514/557 |
| 4,078,061 | 3/1978 | Benson ................................ 514/178 |
| 4,224,339 | 9/1980 | Van Scott ............................. 424/70 |
| 4,234,599 | 11/1980 | Van Scott ........................... 514/451 |
| 4,372,297 | 2/1983 | Fahim ................................. 424/145 |
| 4,536,399 | 8/1985 | Flynn .................................... 424/69 |

Primary Examiner—Thurman K. Page
Assistant Examiner—P. Prater
Attorney, Agent, or Firm—Charles C. Logan, II

[57] ABSTRACT

A composition comprising squalene and saturated normal aliphatic hydrocarbons which is very effective in the treatment of acne, minor skin irritations and minor skin wounds, burns, inflammation and soreness when applied topically to the skin. Basically, the product comprises from about 5 to 40 volume percent squalene and from about 5 to 25 volume percent n-decane, n-dodecane or mixtures thereof with the balance being normal aliphatic hydrocarbons with chain lengths in the C10 to C35 range or a water-polysorbate emulsion. If desired, certain other ingredients such as zinc oxide or a filler may be added to the mixture. The product may be applied as a spray, cream or gel.

20 Claims, No Drawings

PRODUCT AND METHOD FOR THE TREATMENT OF ACNE AND OTHER SKIN DISORDERS

BACKGROUND OF THE INVENTION

This invention relates in general to skin care products and, more specifically, to a product for treating acne and other skin disorders.

A great many different cosmetic and skin treatment products are available. Many are very complex formulations containing a wide variety of ingredients. For example, a commercially available moisturizing cream lists as its ingredients: water, mineral oil, petrolatum, glycerin, isohexadecane, ozokerite, microcrystalline wax, lanolin, alcohol, paraffin, magnesium sulfate, dodecyl oleate, octyl dodecanol, aluminum stearate, fragrance, methylchloroisothiazolinone, methylisothiazolinone, citric acid, and magnesium stearate. Another popular skin healing cream contains, in addition to zinc oxide as the active ingredient, "Norwegian cod liver oil, rich in natural vitamins A and D, plus lanolin, petrolatum, talcum, . . . ". Studies have shown, however, that many ingredients in currently marketed cosmetic products are often comedogenic or irritating to the skin of many people. For example, J. E. Fulton in "Let's Talk Cosmetics", Acne Research Institute Inc., 1977, mentions as strongly comedogenic PEG 16 lanolin, acetylated lanolin, ethoxylated lanolin, stearic acid isopropyl myristate, myristyl myristate, isopropyl isostearate, hexadecyl alcohol, oleyl alcohol, cocoa butter, coconut butter, many vegetable oils, sodium lauryl sulfate, tocopherol (vitamin E), among others. Thus, the very products which are intended to protect or heal the skin are often the cause of further irritation and comedones (blackheads). Also, some people have allergic reactions to some ingredients in these prior products.

Mineral oil and petrolatum are usually considered to be neither comedogenic nor irritating to the skin. However, mineral oil and petrolatum are very ill defined products, being mixtures of paraffinic hydrocarbons. Lower molecular weight components, such as hexane, heptane or octane are actually highly irritating substances and may cause "oil acne". They have a defattening action on the skin which may lead to irritation and infection. Kerosene which is sometimes used as a solvent in cosmetics is a mixture of petroleum hydrocarbons having chain lengths of from about 10 to 18, isolated by fractional distillation. It has a defattening action on the skin and may give rise to irritation, as mentioned in the Merck Index, 10th Edition, 761, 1983.

Thus, there is a continuing need for improved skin care products which prevent and treat acne and other skin irritations without adding to the skin irritation or causing allergic or other detrimental reactions.

SUMMARY OF THE INVENTION

The above-noted problems, and others, are overcome by the product of this invention which basically comprises from above 5 to 40 volume percent squalene and about 5 to 25 volume percent n-decane and/or n-dodecane. The balance may comprise long-chain saturated normal aliphatic hydrocarbons (n-alkanes) or a water-polysorbate emulsion. Generally, the n-alkanes have the formula $C_xH_{x+1}$ where x is from 10 to 35. Within that range, best results with oily skin tend to achieved where x is from about 10 to 18, while with normal or dry skin longer chain lengths are preferred, generally hydrocarbons having x in the 18 to 26 range.

Variable proportions of other active ingredients such as zinc oxide (up to about 50 percent by weight based on the weight of the mixture before addition) or inert fillers (up to about 20 volume percent, based on mixture volume before addition) such as titanium dioxide, starch, modified celluloses, etc. may replace a portion of the hydrocarbons, if desired.

DETAILED DESCRIPTION OF THE INVENTION

Normal skin contains odd and even numbered saturated normal aliphatic hydrocarbons from C18 to C35 at an overall concentration of about 3.9%, with larger amounts of the longer chain length hydrocarbons. In addition the skin contains squalene in concentrations of about 4.9%. Squalene, 2,6,10,15,19,23-hexamethyl-2,6,10,14,18,22-tetracosahexaene, is an unsaturated hydrocarbon with six unconjugated double bonds. The skin contains squalene and those n-alkanes evenly distributed through the skin. The n-alkanes are very inert and not easily degraded by bacteria. Squalene is known to have bactericidal properties. Squalenes are described in detail in "Final Report on Safety Assessment of Squalane and Squalene", Journal of the American College of Toxicology, Special Issue, Vol. 1, No.2, 1982, edited by M. S. Christian.

Because of its bactericidal and fungicidal properties, it appears that squalene plays a role in protecting human skin against infections. Skin may lose its ability to withstand infectious agents either if too little squalene is produced by, or transported to, the skin or if squalene is removed through the use of certain cleansing or defattening agents. Squalene can be lost through the use of external creams or lotions containing fatty substances or may be destroyed by exposure to environmental agents causing accelerated oxidation.

Facial skin is especially vulnerable to the loss of the n-alkanes and squalene because it is frequently exposed to soaps, creams of all kinds, make-up, powders pigments, perfumes and lotions. Also, the face is constantly exposed to airborne pathogens, dust and other environmental factors. The net effect of this combined assault on facial skin is a derangement of the skins natural lipid composition, leading to overreaction of sebaceous glands, changes in the normal moisture content, increasing fragility of the epidermis and a resulting greater vulnerablility to infection.

I have found that an effective treatment for acne and other minor skin irritations should change the lipid composition of the skin to diminish the levels of biodegradable lipids and to increase the concentration of nonbiodegradable and bactericidal constituents. Topical lotions comprising squalene, dodecane and/or n-decane and other long chain n-alkanes provide these desired characteristics.

The precise composition of the product may be varied, depending on whether it is to be applied to dry or oily skin and whether the lesion is superficial or nested in deeper epidermal layers. For dry skin, it should preferably have no defattening action, using n-alkanes having chain lengths in the 18 to 26 range with some n-decane and/or n-dodecane. With oily or fatty skin, it is preferable to use a product with a locally defattening action, having a medium chain length n-alkane, in the C10 to C18 range. The n-alkanes have a good penetrating action and transport squalene into deeper layers of the skin, which is especially desirably for deeper lesions. The n-alkanes also seem to function as inhibiters of the biosynthesis of lipids in sebaceous cells. Thus, the combination of squalene with n-alkanes appears to produce a synergistic effect, in the inhibition of lipid biosyntheses in the skin, the defattening action and the bactericidal activity. Topical application of these products alters the local lipid concentration, introduces inert inhibiters of lipid biosynthesis and supplies additional quantities of a normal constituent of human skin with bactericidal activity. As detailed below, clinical tests show that this results in rapid reduction of acneform lesions, with noticeable improvements occurring within a few hours after the first application.

Any suitable quantity of the product may be applied to the skin at each application. Only a thin film, lightly massaged into the skin, is needed. To an extent, heavier applications and more frequent applications may speed up healing somewhat;.

Application of this product appears to accelerate wound healing, stimulate epidermal growth, reduce inflammatory conditions of various etiologies and to prevent secondary infections. The product also has a preventative effect in making normal skin more resistant to infection and the development of comedones. The n-alkane component furthermore increases the elasticity of the skin and normalizes its moisture content. Generally, best results are obtained with n-alkanes having chain lengths between about C10 and C26, although in cases of unusual skin softness, n-alkanes up to C35 may be desirable in small quantities.

Excellent results are obtained where the product contains from about 5 to 40 volume percent squalene. Within that range, optimum results are generally obtained with about 33 volume percent squalene, although that will vary slightly depending on skin type and other conditions. The balance of the product is ordinarily an n-alkane having the formula $C_xH_{2x-1}$ where "x" is from 10 to 35. Best overall results are obtained where about 33 volume percent of the product is n-decane and/or n-dodecane (x there being 10 and 12) while for the balance of the n-alkane, x is from 10 to 26. For oily skin, it is generally advantageous to limit x to from 10 to 18, while for dry skin best results are obtained with most of the remainder n-alkane having x in the 18 to 26 range.

If desired, active ingredients such as zinc oxide or inert ingredients such as fillers, gelling agents, etc. can be substituted for a quantity of the n-alkane, although in general added active agents are unnecessary and often undesirable. For some purposes, it may be desirable to add an amount of finely dispersed zinc oxide powder equal to about 50 weight percent to one of the product mixtures described above. The resulting product may be applied as a lotion or cream, or may be mixed with an inert propellant and sprayed onto the skin. Also, up to about 20 weight percent of an inert filler to the product.

In some cases, a water base cream or lotion may be preferred. Typically, about 10 parts by weight squalene is mixed with about 5 parts n-alkane, about 55 parts water and about 30 parts of a polysorbate emulsifying agent of the sort available from Atlas Chemical under the Tween 80 trademark. The quantity of water and polysorbate is varied as desired to produce a cream of the desired consistency.

Details of the invention, and of certain preferred embodiments thereof will be further understood upon reference to the following Examples. Parts are by weight and percentages are by volume unless otherwise indicated.

EXAMPLE I

A male subject had been suffering from acne vulgaris for about 10 years with little relief other than from antibiotics to which he had now developed an allergy. He has tried most of the acne lotions and creams on the market without significant success. His face is washed and dried, then a mixture of about 33 volume percent squalene, about 33 volume percent n-dodecane and about 33 volume percent n-tetradecane is evenly applied to his face several times daily for several weeks. Healing of acne lesions becomes apparent within hours and healing is complete within a few days.

EXAMPLE II

A person having severe acne lesions and small scratches on both sides of the face and an oily skin is treated as follows. The face is carefully washed and dried. One side is treated three times daily with the mixture described in Example I and the other with a mixture of 20 volume percent squalene, 10 volume percent n-decane, 10 volume percent n-dodecane and 60 volume percent mixed n-alkanes in the C22 to C26 range. After several days, both sides of the person's face have improved dramatically, with the side treated with the mixture according to Example I showing the greatest improvement. The shorter chain length n-alkanes are seen to perform better on oily skin.

EXAMPLE III

The experiment of Example II is repeated with a person having severe acne lesions and a very dry skin. Again, both sides show a dramatic decrease in acne lesions. The side using the mixture including longer chain hydrocarbons is softer than the other side, indicating that long chain n-alkanes have advantages with dry skin.

EXAMPLE IV

The face of a woman who has developed severe acneform facial lesions is treated as follows. A mixture of about 10 parts by weight squalene, about 5 parts by weight mixed n-decane and longer chain n-alkanes, about 30 parts Tween 80 emulsifier from Atlas Chemical and about 55 parts water is prepared, forming a thick, smooth cream. Twice each day, the cream is spread lightly on the skin eruptions. Within days, almost all red lesions have disappeared and the skin is smooth and soft.

EXAMPLE V

The treatment as described in Example I is continued, except that the quantity of squalene in the mixture is gradually reduced from about 33 volume percent to about 2 volume percent over a period of several weeks. While the appearance of the face is still better than without treatment, the effectiveness is reduced and less control of the acne lesions is apparent at the lower concentrations. Increasing the concentration above 33 volume percent seems to provide little improvement. Over a long period of time, it appears that lower concentrations may be used, if applied more often and in thicker layers, but that an optimum combination of convenience and effectiveness occurs at around 30 to 33 volume percent squalene.

EXAMPLE VI

About 10 parts by weight squalene, about 2 parts n-dodecane, and about 2 parts n-tetradecane are mixed with about 30 parts Tween 80 polysorbate emulsifier. Water is mixed in gradually until the desired consistency is reached. The mixture is then applied twice a day to the face of a person having a number of acne lesions together with moderate sunburn. The sunburn is relieved rapidly and the acne lesions are dramatically reduced within days.

EXAMPLE VII

A hydrocarbon-squalene spray for topical applications is prepared by mixing together about 30 volume percent squalene, about 20 volume percent of n-dodecane and about 10 volume percent n-tetradecane, then mixing in about 40 volume percent Freon perfluorocarbon gas in a pressurized vessel. A light coating is sprayed on the face of a person having dry, flaky skin with sever acne. Improvement is noted within hours and after a few days of twice daily applications the acne lesions are much improved and the skin is soft, resilient and smooth.

While certain specific ingredients, proportions and methods are described in the above examples which point out certain preferred embodiments of my invention, these may be varied, where suitable, with similar results. Other variations, applications and ramifications of this invention will occur to those skilled in the art upon reading this disclosure. Those are intended to be included within the scope of this invention as defined in the appended claims.

I claim:

1. A product for the treatment and prevention of acne and other skin disorders which comprises:
   about 5 to 40 volume percent squalene;
   about 5 to 25 volume percent n-dodecane, n-decane or mixtures thereof; and
   the balance being selected from saturated normal aliphatic hydrocarbons having the formula $C_xH_{2x+1}$, where "x" is from 10 to 26.

2. The product according to claim 1 wherein "x" is from 10 to 18 and said product is especially adapted for use with oily skin.

3. The product according to claim 1 wherein "x" is primarily from 18 to 26, with the balance being 12 and said product is especially adapted for use with normal to dry skin.

4. The product according to claim 1 further including zinc oxide in a volume up to equal to that of the other ingredients combined.

5. The product according to claim 1 wherein up to about 20 volume percent of said hydrocarbon is replace with an inert filler.

6. The product according to claim 1 further including an effective quantity of an inert gas under pressure to form a sprayable mixture.

7. A product for the treatment and prevention of acne and other skin disorders which comprises:
   about 33 volume percent squalene;
   about 33 volume percent of an n-alkane selected from the group consisting of n-decane, n-dodecane and mixtures thereof; and
   about 33 volume percent tetradecane.

8. The product according to claim 7 having up to 50 weight percent zinc oxide, based on the weight of the product prior to addition of the zinc oxide.

9. A product for the treatment and prevention of acne and other skin disorders which comprises:
   about 10 parts by weight squalene;
   about 2 parts by weight of an n-alkane selected from the group consisting of n-decane, n-dodecane and mixtures thereof;
   about 2 parts by weight n-tetradecane;
   about 30 parts of a polysorbate emulsifying agent; and
   sufficient water to provide a cream of desired consistency.

10. The product according to claim 9 further including up to about 21 parts by weight zinc oxide.

11. The product according to claim 9 further including up to about 10 parts by weight of an inert filler.

12. The method of treating and preventing acne and other skin disorders which comprises the steps of:
    providing a mixture comprising from about 5 to 40 volume percent squalene, about 5 to 25 volume percent of an n-alkane selected from the group consisting of n-decane, n-dodecane and mixtures thereof and the balance selected from the group consisting of saturated normal aliphatic hydrocarbons having the formula $C_xH_{2x2}$ where "x" is from 10 to 35 and water-polysorbate emulsions; and
    applying an effective quantity of said mixture to the skin of a human being.

13. The method according to claim 12 including the further step of mixing up to about 50 weight percent of zinc oxide to said mixture prior to application.

14. The method according to claim 12 further including adding a pressurized inert propellant gas to said mixture under pressure and applying said mixture by spraying.

15. The method of treating and preventing acne and other skin disorders which comprises the steps of:
    mixing together about 10 parts by weight squalene, about 2 parts by weight of an n-alkane selected from the group consisting of n-deane, n-dodecane and mixtures thereof, about 2 parts by weight n-tetradecane, about 30 parts by weight of a polysorbate emulsifying agent and sufficient water to provide a cream of desired consistency; and
    applying an effective quantity of said mixture to the skin of a human being.

16. The method according to claim 15 further including adding up to 50 volume percent zinc oxide, based on the volume of said mixture, to said mixture prior to application.

17. The method according to claim 15 further including adding a pressurized inert propellant gas to said mixture under pressure and applying said mixture by spraying.

18. The method of treating and preventing acne and other skin disorders which comprises the steps of:
    mixing together about 33 volume percent squalene, about 33 volume percent of an n-alkane selected from the group consisting of n-decane, n-dodecane and mixtures thereof and about 33 volume percent n-tetradecane; and
    applying an effective quantity of said mixture to the skin of a human being.

19. The method according to claim 18 further including adding up to 50 weight percent powdered zinc oxide, based on the weight of said mixture, to said mixture prior to application.

20. The method according to claim 18 further including adding a pressurized inert propellant gas to said mixture under pressure and applying said mixture by spraying.

* * * * *

UNITED STATES PATENT AND TRADEMARK OFFICE
CERTIFICATE OF CORRECTION

PATENT NO. : 4,849,211
DATED : July 18, 1989
INVENTOR(S) : Gerhard N. Schrauzer It is certified that error appears in the above—identified patent and that said Letters Patent is hereby corrected as shown below:

Column 1, line 66, the formula reading "-CxHx+1-" should read -- $-C_xH_{2x+2}-$ --.

Column 3, line 39, the formula reading "-CxHx+1-" should read -- $-C_xH_{2x+2}-$ --.

Column 5, line 42, the formula reading "-CxHx+1-" should read -- $-C_xH_{2x+2}-$ --.

Column 6, line 22, the formula reading "-CxH 2x2-" should read -- $-C_xH_{2x+2}-$ --.

Column 6, line 38, the word "-n-deane-" should read -- -n-decane- --.

Signed and Sealed this

Twenty-first Day of May, 1991

*Attest:*

HARRY F. MANBECK, JR.

*Attesting Officer*  *Commissioner of Patents and Trademarks*